(12) United States Patent
Gralla et al.

(10) Patent No.: US 8,653,313 B2
(45) Date of Patent: Feb. 18, 2014

(54) PROCESS FOR PREPARING A PHENYLCYCLOHEXANE

(75) Inventors: Gabriele Gralla, Mannheim (DE); Gunnar Heydrich, Limburgerhof (DE)

(73) Assignee: BASF SE (DE)

( * ) Notice: Subject to any disclaimer, the term of this patent is extended or adjusted under 35 U.S.C. 154(b) by 168 days.

(21) Appl. No.: 13/287,540

(22) Filed: Nov. 2, 2011

(65) Prior Publication Data
US 2012/0108874 A1    May 3, 2012

Related U.S. Application Data

(60) Provisional application No. 61/409,128, filed on Nov. 2, 2010.

(51) Int. Cl.
| | | |
|---|---|---|
| *C07C 15/02* | (2006.01) | |
| *C07C 13/465* | (2006.01) | |
| *C07C 5/10* | (2006.01) | |

(52) U.S. Cl.
USPC ............ 585/400; 585/266; 585/269; 585/270

(58) Field of Classification Search
USPC ...................................................... 585/400
See application file for complete search history.

(56) References Cited

U.S. PATENT DOCUMENTS

| | | |
|---|---|---|
| 2,471,134 A | 5/1949 | Wright |
| 3,387,048 A | 6/1968 | Rylander et al. |
| 3,796,763 A * | 3/1974 | Hartung .................. 585/267 |
| 4,230,533 A | 10/1980 | Giroux |
| 5,037,793 A * | 8/1991 | Toussaint et al. ............. 502/308 |
| 5,530,127 A | 6/1996 | Reif et al. |
| 7,960,593 B2 * | 6/2011 | Gralla et al. .................. 568/830 |
| 2011/0295024 A1 * | 12/2011 | Gralla et al. .................. 549/416 |

FOREIGN PATENT DOCUMENTS

| | | |
|---|---|---|
| CA | 1222717 A1 | 6/1987 |
| CA | 1242309 A1 | 9/1988 |
| CN | 1800121 A | 7/2006 |
| DE | 937 950 C | 1/1956 |
| DE | 2 125 473 A1 | 12/1972 |
| EP | 0 122 367 A2 | 10/1984 |
| EP | 126 288 A2 | 11/1984 |
| EP | 133 510 A1 | 2/1985 |
| EP | 0 394 842 A1 | 10/1990 |
| EP | 696572 A1 | 2/1996 |
| WO | WO-93/16972 A1 | 9/1993 |

OTHER PUBLICATIONS

Sinnott, R.K. (2005). Coulson and Richardson's Chemical Engineering vol. 6—Chemical Engineering Design (4th Edition).. Elsevier.*

* cited by examiner

*Primary Examiner* — In Suk Bullock
*Assistant Examiner* — Philip Louie
(74) *Attorney, Agent, or Firm* — Novak Druce Connolly Bove + Quigg LLP

(57) ABSTRACT

The present invention relates to an improved process for preparing a substituted or unsubstituted phenylcyclohexane by catalytic hydrogenation of a substituted or unsubstituted biphenyl.

16 Claims, No Drawings

PROCESS FOR PREPARING A PHENYLCYCLOHEXANE

CROSS-REFERENCE TO RELATED APPLICATIONS

This application claims the benefit of U.S. Provisional Application 61/409,128, filed Nov. 2, 2010, which is incorporated by reference.

BACKGROUND OF THE INVENTION

The present invention relates to an improved process for preparing a substituted or unsubstituted phenylcyclohexane by catalytic hydrogenation of a substituted or unsubstituted biphenyl.

The preparation of phenylcyclohexane by full hydrogenation of one phenyl ring of the biphenyl is known in principle.

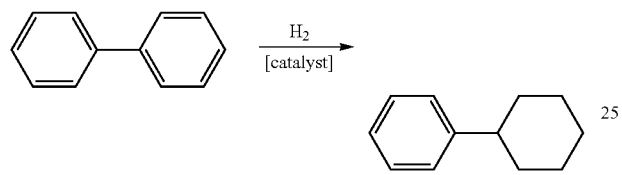

By-products formed usually always include, inter alia, bicyclohexyl which forms an azeotrope with phenylcyclohexane.

In Journal of the Chemical Society 1951, pages 1371-1372, I. Goodman describes the preparation of phenylcyclohexane by catalytic hydrogenation of biphenyl to phenylcyclohexane in ethanol in the presence of Raney nickel.

Tetrahedron Letters 2000, No. 41, pages 5865-5868, describes the preparation of phenylcyclohexane by hydrogenation of biphenyl in the presence of Raney nickel-aluminum alloys at a temperature of 90° C.

DE 937 950 discloses a process for the catalytic hydrogenation of biphenyl to phenylcyclohexane using a nickel- and cobalt-free copper-chromium catalyst at a temperature of about 240-260° C.

U.S. Pat. No. 3,387,048 discloses a process for preparing phenylcyclohexane by hydrogenation of biphenyl with addition of the solvent cyclohexane. A suitable catalyst is indicated as being 5% palladium on carbon.

DE 2 125 473 relates to catalysts comprising cobalt oxide or a mixture of cobalt oxides, e.g. $Co_3O_4$ and CoO, for the partial hydrogenation of biphenyl derivatives.

WO 93/16972 relates to catalysts for the hydrogenation of polycyclic and monocyclic aromatics such as alkyl-substituted benzene derivatives and substituted biphenyls, with the catalysts comprising ruthenium.

CN 1800121 discloses a process for preparing phenylcyclohexane by hydrogenation of biphenyl in the presence of nickel-aluminum catalysts.

EP 0 394 842 relates to catalysts for the hydrogenation of aliphatic unsaturated compounds, where the catalysts comprise nickel and copper and are characterized by a content of from 20 to 75% by weight of nickel oxide, from 10 to 75% by weight of zirconium dioxide and from 5 to 50% by weight of copper oxide, in each case based on the oxidic, unreduced catalyst. The catalysts are particularly suitable for the hydrogenation of the industrially important compounds 2-butyne-1,4-diol, 2-butene-1,4-diol and 2-ethylhexen-2-al.

Some of the above-described processes for preparing substituted or unsubstituted phenylcyclohexane use catalysts which are either not easy to handle on an industrial scale or are not readily available. Furthermore, the known processes in some cases display an unsatisfactory selectivity to the target product and/or a space-time yield which is too low.

DETAILED DESCRIPTION OF THE INVENTION

In the light of this prior art, it was an object of the present invention to provide a process which makes it possible to prepare phenylcyclohexane by hydrogenation of biphenyl under economically optimized conditions. The process should be able to be carried out on an industrial scale in a readily managed manner in process engineering terms and lead to the desired product in a high chemical yield and high selectivity using cheap catalysts. The formation of bicyclohexyl should be avoided as far as possible since, as mentioned at the outset, bicyclohexyl and phenylcyclohexane form an azeotrope which reduces the yield of pure phenylcyclohexane in a purification by distillation.

This object is achieved by a process for preparing a substituted or unsubstituted phenylcyclohexane of the formula I

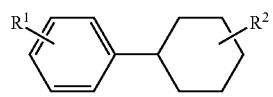

I by catalytic hydrogenation of a substituted or unsubstituted biphenyl of the formula II

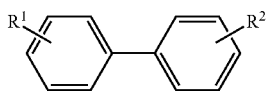

II where $R^1$ is hydrogen and $R^2$ is hydrogen or phenyl, or $R^1$ is a $C_1$-$C_4$-alkyl radical and $R^2$ is hydrogen, or $R^1$ and $R^2$ are identical and are each phenyl or the same $C_1$-$C_4$-alkyl radical, where $R^1$ and $R^2$ are both simultaneously located in the respective ortho, meta or para positions of the two phenyl rings of the biphenyl of the formula II,
in the presence of hydrogen and a catalyst comprising
    from 30 to 70% by weight of oxygen-comprising compounds of nickel, calculated as NiO,
    from 15 to 45% by weight of oxygen-comprising compounds of zirconium, calculated as $ZrO_2$,
    from 5 to 30% by weight of oxygen-comprising compounds of copper, calculated as CuO,
    from 0.1 to 10% by weight of oxygen-comprising compounds of molybdenum, calculated as $MoO_3$, and
    0 to 10% by weight of further components,
where the figures in % by weight are based on the dry, unreduced catalyst.

In the process of the invention, a biphenyl of the formula II,

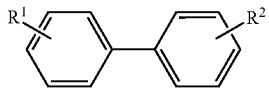

II where $R^1$ is hydrogen and $R^2$ is hydrogen or phenyl, or $R^1$ is a $C_1$-$C_4$-alkyl radical and $R^2$ is hydrogen, or $R^1$ and $R^2$ are identical and are each phenyl or the same $C_1$-$C_4$-alkyl radical, where $R^1$ and $R^2$ are both simultaneously located in the respective ortho, meta or para positions of the two phenyl rings of the biphenyl of the formula II, is used as starting material.

The $C_1$-$C_4$-alkyl radical is methyl, ethyl, n-propyl, isopropyl, n-butyl, sec-butyl, tert-butyl or 2-methyl-1-propyl, preferably methyl or tert-butyl, in particular methyl.

Examples of biphenyls of the formula II are, inter alia,

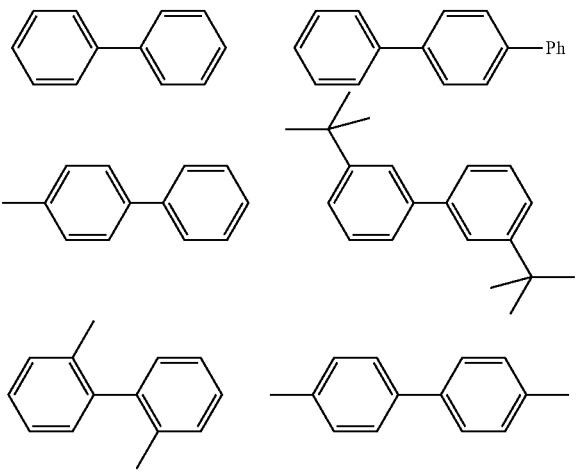

The biphenyl of the formula II is preferably unsubstituted biphenyl, i.e. $R^1$ and $R^2$ are each hydrogen.

Preference is therefore given to a process according to the invention as described above where $R^1$ and $R^2$ are hydrogen, i.e. a process for preparing phenylcyclohexane of the formula Ia

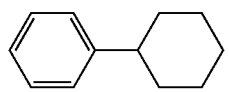

by catalytic hydrogenation of unsubstituted biphenyl of the formula IIa.

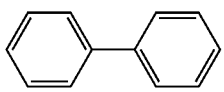

The biphenyls of the formula II which can be used in the process of the invention are usually commercially available, for example simple biphenyl which is obtained from the distilled oils of hard coal tar. The substituted biphenyls can be obtained, for example, by aryl-aryl coupling reactions known to those skilled in the art, for example Suzuki coupling.

The process of the invention is carried out in the presence of hydrogen and in the presence of a heterogeneous catalyst, with the heterogeneous catalyst to be used comprising from 30 to 70% by weight, preferably from 40 to 60% by weight, of oxygen-comprising compounds of nickel, calculated as NiO, from 15 to 45% by weight, preferably from 20 to 40% by weight, of oxygen-comprising compounds of zirconium, calculated as $ZrO_2$, from 5 to 30% by weight, preferably from 10 to 25% by weight, of oxygen-comprising compounds of copper, calculated as CuO, and from 0.1 to 10% by weight, preferably from 0.5 to 5% by weight, of oxygen-comprising compounds of molybdenum, calculated as $MoO_3$, optionally together with further components in an amount of from 0 to 10% by weight, preferably from 0 to 5% by weight, for example graphite. Here, the figures in % by weight are based on the dry, unreduced catalyst.

Since the concentrations indicated are each, unless indicated otherwise, based on the catalytically active composition of the catalyst, the catalytically active composition of the catalyst will hereinafter be defined as the sum of the masses of the catalytically active constituents zirconium, nickel, copper and molybdenum in the catalyst, in each case calculated as $ZrO_2$, NiO, CuO and $MoO_3$, respectively, after the last heat treatment and before reduction with hydrogen.

In a preferred embodiment, the process of the invention is carried out using catalysts comprising
from 45 to 55% by weight of oxygen-comprising compounds of nickel, calculated as NiO,
from 25 to 35% by weight of oxygen-comprising compounds of zirconium, calculated as $ZrO_2$,
from 13 to 20% by weight of oxygen-comprising compounds of copper, calculated as CuO,
from 1 to 3% by weight of oxygen-comprising compounds of molybdenum, calculated as $MoO_3$, and
from 0 to 5% by weight of further components,
where the figures in % by weight add up to 100% by weight and are based on the dry, unreduced catalyst. Very particular preference is given according to the invention to catalysts which consist of the abovementioned components in the proportions by weight likewise indicated above.

A catalyst which is very particularly preferred for use in the process of the invention comprises from 49 to 53% by weight of NiO, from 15 to 19% by weight of CuO, from 28 to 32% by weight of $ZrO_2$ and from 1 to 2% by weight of $MoO_3$ and optionally from 0 to 3% by weight of further components such as graphite, where the proportions by weight selected in each case for the individual components are based on the dry, unreduced catalyst and add up to 100% by weight. Such catalysts are known and can be prepared, for example, as described in EP 0 696 572.

The catalysts which can be used according to the invention can be produced, for example, by use of precipitation methods. Thus, for example, they can be obtained by coprecipitation of the nickel and copper components from an aqueous salt solution comprising these elements by means of mineral bases in the presence of a slurry of a sparingly soluble, oxygen-comprising zirconium compound and subsequent washing, drying and calcination of the precipitate obtained. As sparingly soluble, oxygen-comprising zirconium compounds, it is possible to use, for example, zirconium dioxide, zirconium oxide hydrate, zirconium phosphates, borates and silicates. The slurries of the sparingly soluble zirconium compounds can be produced by suspending finely divided powders of these compounds in water with vigorous stirring. These slurries are advantageously obtained by precipitating the sparingly soluble zirconium compounds from aqueous zirconium salt solutions by means of mineral bases.

The catalysts which can be used according to the invention are preferably produced by coprecipitation (mixed precipitation) of all their components. For this purpose, an aqueous salt solution comprising the catalyst components is advantageously admixed, hot and while stirring, with an aqueous mineral base, in particular an alkali metal base, for example sodium carbonate, sodium hydroxide, potassium carbonate or potassium hydroxide, until precipitation is complete. The type of salts used is generally not critical; since the water solubility of the salts is of primary importance in this procedure, a criterion is the good water solubility required for producing these comparatively highly concentrated salt solutions. It is considered to be self evident that naturally only salts having anions which do not lead to interference, whether by causing undesirable precipitations or by making precipitation difficult or preventing it entirely by formation of complexes, are chosen in selecting the salts of the individual components.

Catalysts which can be used according to the invention and have particularly advantageous properties can be obtained by precipitating part of the zirconium component of the catalyst, advantageously from an aqueous zirconium salt solution, separately in a precipitation apparatus by addition of aqueous mineral bases. The remainder of the zirconium component of the catalyst together with the other catalytically active components can then be precipitated on to the resulting, preferably freshly precipitated, zirconium oxide hydrate in a coprecipitation as described above. Here, it is generally found to be particularly advantageous to preprecipitate from 10 to 80% by weight, preferably from 30 to 70% by weight and in particular from 40 to 60% by weight, of the total amount of zirconium in the catalytically active composition.

The precipitates obtained in these precipitation reactions are generally chemically nonuniform and comprise, inter alia, mixtures of the oxides, hydrated oxides, hydroxides, carbonates and insoluble and basic salts of the abovementioned metals. It may be found to be advantageous in terms of the filterability of the precipitates for them to be aged, i.e. for them to be left to stand for some time after the precipitation, optionally hot or with air being passed through.

The precipitates obtained by these precipitation processes can be processed further in a conventional way to give the catalysts which can be used according to the invention. After washing, they are generally dried at from 80 to 200° C., preferably from 100 to 150° C., and then calcined. Calcination is generally carried out at temperatures in the range from 300 to 800° C., preferably from 400 to 600° C., in particular from 450 to 550° C.

After calcination, the catalyst is advantageously conditioned, either by bringing it to a particular particle size by milling or by mixing it after milling with shaping aids such as graphite or stearic acid, pressing it by means of a tableting press to give shaped bodies and heat treating it. The temperatures here generally correspond to the temperatures in the calcination.

The catalysts produced in this way comprise the catalytically active metals in the form of a mixture of their oxygen-comprising compounds, i.e. in particular as oxides and mixed oxides.

The catalysts produced in this way can be stored and used as such. Before use as catalysts in the process of the invention, they are usually prereduced. However, they can also be used without prereduction, in which case they are then reduced by the hydrogen present in the reactor under the conditions of the hydrogenation according to the invention. For prereduction, the catalysts are generally firstly exposed to a nitrogen/hydrogen atmosphere at from 150 to 200° C. for a period of from 12 to 20 hours and subsequently treated in a hydrogen atmosphere at from 200 to 300° C. for up to about 24 hours. In this prereduction, part of the oxygen-comprising metal compounds present in the catalysts is usually reduced to the corresponding metals, so that these are present together with the various oxygen compounds in the active form of the catalyst.

In general, the catalysts used according to the invention are preferably used in the form of all-active catalysts. The term "all-active catalysts" refers to a catalyst which, in contrast to a supported catalyst, consists entirely of catalytically active compositions. All-active catalysts can be used by introducing the catalytically active composition which has been milled to a powder into the reaction vessel or by arranging the catalytically active composition after milling, mixing with shaping aids, shaping and heat treatment as shaped catalyst body, for example as spheres, cylinders, pellets, rings, spirals, extrudates and the like, in the reactor.

In a preferred embodiment of the process of the invention, the selected catalyst, which is a heterogeneous catalyst, is used in the form of a fixed-bed catalyst in the catalytic hydrogenation, i.e. in the hydrogenation step of the process of the invention.

To carry out the process of the invention, the starting material as described above, namely a biphenyl of the formula II, is brought into contact with hydrogen and the chosen catalyst. The hydrogen can be used in undiluted form, usually in a purity of about 99.9% by volume, or in diluted form, i.e. in the form of mixtures with inert gases such as nitrogen or argon. Hydrogen is preferably used in undiluted form.

The catalytically active hydrogenation can be carried out successfully without addition of solvent or in the presence of organic solvents which are inert under the reaction conditions, for example methanol, ethanol, isopropanol, hexane, heptane, cyclohexane and the like. The hydrogenation is preferably carried out without addition of solvent.

In the process of the invention, the hydrogenation of the biphenyl of the formula II can be carried out under a hydrogen pressure (absolute) in the range from 1 to 200 bar, preferably from 2 to 150 bar, particularly preferably from 4 to 80 bar, very particularly preferably from 5 to 50 bar. As reaction temperature for carrying out the hydrogenation, it is advantageous to choose a temperature in the range from 50 to 250° C., preferably from 100 to 180° C., very particularly preferably from 110 to 160° C.

In industrial practice, the process is generally carried out by supplying the biphenyl of the formula II which is to be reacted to the catalyst which is usually present in a preferably externally heated fixed-bed reactor, for example a tube reactor, autoclave or shell-and-tube reactor, at the desired reaction temperature and the desired pressure. Here, it is usual to supply the catalyst with from 0.1 to 1.0 kg, preferably from 0.1 to 0.6 kg and particularly preferably from 0.2 to 0.4 kg, of the biphenyl of the formula II per kg of catalyst and per hour. Here, it can be advantageous to heat the biphenyl of the formula II to be used before it is fed into the reaction vessel or the reactor, preferably to the reaction temperature.

The reactor can be operated either in the upflow mode or in the downflow mode, i.e. the starting materials can be passed through the reactor either upward from below or downward from the top. The hydrogenation step in the process of the invention can be carried out either batchwise or continuously. In both cases, unreacted starting material can be circulated together with the hydrogen.

The hydrogenation step in the process of the invention can also be carried out stepwise in a cascade of a plurality of, i.e. from 2 to generally 4, preferably 2 or 3 and particularly preferably 2, reactors, preferably fixed-bed reactors, connected in series. Here, the main conversion of the reaction is achieved in the first reactor, usually referred to as main reactor, under the above-described reaction conditions and the crude product obtained is fed to a second reactor, usually referred to as after-reactor, in which the as yet unreacted starting material is at least substantially converted in a manner according to the invention into phenylcyclohexane of the formula I. Here, the reaction conditions can be selected independently of one another, preferably in the abovementioned ranges.

In the process of the invention, the hydrogenation can be carried out batchwise, semicontinuously or fully continuously. The catalytic hydrogenation in the process of the invention is preferably carried out continuously, in particular fully continuously, with the starting materials being introduced continuously into the reactor and the reaction mixture or reaction product obtained being discharged continuously from the reactor.

The reaction mixture or reaction product obtained in the hydrogenation step of the process of the invention can, after intermediate buffering in a vessel, be purified by fractional distillation, preferably by fractional distillation under reduced pressure, in order to obtain a substituted or unsubstituted phenylcyclohexane of the formula I in a purity of greater than 97% by weight, preferably greater than 98% by weight, based on the total mass. The work-up of the resulting reaction product by distillation can be carried out in a rectification column operated batchwise or continuously. Various industrial embodiments of distillation columns of this type which allow batchwise, semicontinuous or fully continuous distillation are described in the relevant literature.

Accordingly, a preferred variant of the process of the invention comprises working up a reaction product obtained in the catalytic hydrogenation by distillation in a further process step so as to purify the substituted or unsubstituted phenylcyclohexane of the formula I further.

Various process variants are customary according to the prior art for the continuous fractional distillation of multicomponent mixtures. In the simplest case, the feed mixture is separated into two fractions, a low-boiling overhead fraction and a high-boiling bottom fraction. When feed mixtures are separated into more than two fractions, a plurality of distillation columns has to be used in this process variant. To limit the outlay in terms of apparatus, columns having side offtakes for liquid or vapor are used where possible in the fractionation of multicomponent mixtures. However, the use of distillation columns having side offtakes is greatly restricted by the fact that the products taken off at the side offtakes are, according to the prior art, never completely pure. In the case of side offtakes in the enrichment section, where the product is usually taken off in liquid form, the side product still comprises proportions of low-boiling components which should be separated off at the top. A similar situation applies to side offtakes in the stripping section, where the product is usually taken off in vapor form, in the case of which the side product still has proportions of high boilers. The use of conventional side offtake columns is therefore restricted to cases in which contaminated side products are permissible.

One possible remedy is provided by dividing wall columns. This type of column is described, for example, in U.S. Pat. No. 2,471,134; U.S. Pat. No. 4,230,533; EP 0 122 367; EP 0 126 288; EP 0 133 510; Chem. Eng. Technol. 10 (1987) 92-98; Chem.-Ing.-Tech. 61 (1989) No. 1, 16-25; Gas Separation and Purification 4 (1990) 109-114; Process Engineering 2 (1993) 33-34; Trans IChemE 72 (1994) Part A 639-644 and Chemical Engineering 7 (1997) 72-76.

The work-up of the reaction product from the catalytic hydrogenation by distillation is advantageously carried out under reduced pressure at absolute pressures in the range from 1 to 100 mbar, preferably from 5 to 50 mbar. In the case of distillations under reduced pressure, preference is given to using distillation columns having ordered mesh packings having a specific surface area in the range from 250 to 1000 $m^2/m^3$.

In a fractional batch distillation of a reaction output obtained from biphenyl, which output already comprises the undesirable overhydrogenation product bicyclohexyl, bicyclohexyl accompanied by significant proportions of the desired phenylcyclohexane, with which it forms a low-boiling azeotrope, can be separated off in one or more low-boiling fractions. If the bicyclohexyl is distilled off from the still pot, intermediate-boiling pure fractions of phenylcyclohexane can be obtained. The unreacted starting material biphenyl remains at the bottom of the column and part of this can also be distilled off, depending on the amount present and engineering circumstances.

Good use can be made of this effect in industrial practice by carrying out the hydrogenation not to complete conversion of the biphenyl but instead interrupting it as soon as first amounts of bicyclohexyl are found in the reaction output. This can be achieved, for example, in the case of a batch reaction by limiting the reaction time or in the case of a continuous reaction by regulating the reactor temperature or the hydrogenation pressure, i.e. by controlling the conversion of starting material by regulating reaction temperature and/or reaction pressure and/or residence time of the reaction solution in the hydrogenation apparatus.

In a preferred variant of the process of the invention, the hydrogenation is carried out so that from 90 to 95% of the substituted or unsubstituted biphenyl of the formula II is reacted.

The biphenyl-enriched bottoms remaining after the fractional distillation can be recirculated to the reaction, enabling the total yield of phenylcyclohexane to be increased.

In a particularly preferred form of the process of the invention, fractions which are obtained in the work-up of the reaction product from the catalytic hydrogenation by distillation and still comprise biphenyl of the formula II are recirculated in their entirety or in part to the hydrogenation.

The invention is illustrated by the following examples which do not, however, restrict the invention.

EXAMPLES

All experiments were carried out in a 300 ml HC laboratory autoclave provided with a catalyst basket. Sampling was possible via a tube attached at the side. Temperature regulation was effected by means of an external oil bath.

Analysis

GC analysis was carried out by the following method: 30 m DB-WAX, ID.: 0.2 mm, FD. 0.5 µm, Initial Temp.: 200° C., Det. temp.: 250° C.; start 80° C.-3° C./min –200° C./15 min; 240° C./20 min isothermal; amount injected: 0.2 µl; carrier gas He; $t_R$=min; $t_R$ (biphenyl): 25.6; $t_R$ (phenylcyclohexane): 15.4; $t_R$ (phenylcyclohexene): 10.2, 10.6 and 11.0; $t_R$ (bicyclohexyl): 8.7.

Example 1

In a 300 ml laboratory autoclave, 99.6 g of biphenyl were hydrogenated in the presence of 5 g of a catalyst comprising 50% by weight of NiO, 17% by weight of CuO, 30.5% by weight of $ZrO_2$ and 1.5% by weight of $MoO_3$ in the form of pellets having a diameter and a height of in each case 3 mm at a hydrogen pressure of 30 bar and a temperature of 130° C. while stirring. After a reaction time of 22 hours, the catalyst was filtered off. The reaction mixture obtained was analyzed by gas chromatography at the times indicated in table 1. The results reported in table 1 were obtained.

TABLE 1

| Running time [h] | Biphenyl | Phenyl-cyclo-hexane GC-% by area | Phenyl-cyclo-hexene | Bicyclohexyl | Temperature [° C.] |
|---|---|---|---|---|---|
| 2 | 98.78 | 1.21 | 0 | 0 | 90 |
| 3 to 6 | 94.88 | 5.12 | 0 | 0 | 90 |
| 7 to 12 | 64.78 | 35.08 | 0 | 0.14 | 120 |
| 13 to 18 | 22.76 | 76.47 | 0 | 0.77 | 130 |
| 19 to 21 | 1.05 | 95.93 | 0.19 | 2.83 | 130 |
| 22 | 0 | 93.76 | 0.31 | 5.93 | 130 |

Example 2

In a 300 ml laboratory autoclave, 100 g of biphenyl were hydrogenated in the presence of 5 g of a catalyst comprising 50% by weight of NiO, 17% by weight of CuO, 30.5% by weight of $ZrO_2$ and 1.5% by weight of $MoO_3$ in the form of pellets having a diameter and a height of in each case 3 mm at a hydrogen pressure of 40 bar and a temperature of 130° C. while stirring. After a reaction time of 14 hours, the catalyst was filtered off. The reaction mixture obtained was analyzed by gas chromatography at the times indicated in table 2. The results reported in table 2 (in each case in GC-% by area) were obtained.

TABLE 2

| Running time [h] | Biphenyl | Phenyl-cyclo-hexane GC-% by area | Phenyl-cyclo-hexene | Bicyclohexyl | Temperature [° C.] |
|---|---|---|---|---|---|
| 5 | 65.17 | 34.36 | 0 | 0.46 | 130 |
| 11 | 21.14 | 77.52 | 0.11 | 1.22 | 130 |
| 13 | 4.31 | 93.10 | 0.16 | 2.46 | 130 |
| 14 | 0.92 | 94.93 | 0.20 | 3.94 | 130 |
| Output | 0 | 94.83 | 0.18 | 4.98 | — |

Example 3

In a 300 ml laboratory autoclave, 100 g of biphenyl were hydrogenated in the presence of 5 g of a catalyst comprising 50% by weight of NiO, 17% by weight of CuO, 30.5% by weight of $ZrO_2$ and 1.5% by weight of $MoO_3$ in the form of pellets having a diameter and a height of in each case 3 mm at a hydrogen pressure of 10 bar and a temperature of 150° C. while stirring. After a reaction time of 17 hours, the catalyst was filtered off. The reaction mixture obtained was analyzed by gas chromatography at the times indicated in table 3. The results reported in table 3 (in each case in GC-% by area) were obtained.

TABLE 3

| Running time [h] | Biphenyl | Phenyl-cyclo-hexane GC-% by area | Phenyl-cyclo-hexene | Bicyclohexyl | Temperature [° C.] |
|---|---|---|---|---|---|
| 6 | 71.73 | 27.87 | 0 | 0.31 | 150 |
| 11 | 41.39 | 58.10 | 0 | 0.43 | 150 |
| 17 | 4.56 | 94.13 | 0 | 0.12 | 150 |
| Output | 0.12 | 95.43 | 0.24 | 4.04 | — |

Example 4

In a 300 ml laboratory autoclave, 100 g of biphenyl were hydrogenated in the presence of 5 g of a catalyst comprising 50% by weight of NiO, 17% by weight of CuO, 30.5% by weight of $ZrO_2$ and 1.5% by weight of $MoO_3$ in the form of pellets having a diameter and a height of in each case 3 mm at a hydrogen pressure of 10 bar and a temperature of 130° C. while stirring. After a reaction time of 48 hours, the catalyst was filtered off. The reaction mixture obtained was analyzed by gas chromatography at the times indicated in table 4. The results reported in table 4 (in each case in GC-% by area) were obtained.

TABLE 4

| Running time [h] | Biphenyl | Phenyl-cyclo-hexane GC-% by area | Phenyl-cyclo-hexene | Bicyclohexyl | Temperature [° C.] |
|---|---|---|---|---|---|
| 9 | 85.62 | 14.29 | 0 | 0 | 130 |
| 15 | 72.38 | 27.46 | 0 | 0.07 | 130 |
| 26 | 45.06 | 54.60 | 0 | 0.05 | 130 |
| 48 | 1.39 | 92.18 | 0.29 | 6.08 | 130 |
| Output | 0 | 92.4 | 0.22 | 7.24 | — |

Comparative Example 5

In a 300 ml laboratory autoclave, 20 g of biphenyl dissolved in 80 g of methanol were hydrogenated in the presence of 5 g of a catalyst comprising 0.5% of Ru on $Al_2O_3$ supports in the form of 4-6 mm spheres at a hydrogen pressure of 30 bar and a temperature of 90-120° C. while stirring. After a reaction time of 12 hours, the catalyst was filtered off. The reaction mixture obtained was analyzed by gas chromatography at the times indicated in table 5. The results reported in table 5 (in each case in GC-% by area) were obtained.

TABLE 5

| Running time [h] | Biphenyl | Phenyl-cyclo-hexane GC-% by area | Phenyl-cyclo-hexene | Bicyclohexyl | Temperature [° C.] |
|---|---|---|---|---|---|
| 1 | 96.43 | 3.57 | 0 | 0 | 90 |
| 3 | 90.49 | 8.95 | 0 | 0.56 | 90 |
| 4 to 6 | 71.99 | 26.49 | 0 | 1.53 | 90 |
| 7 | 56.97 | 40.96 | 0 | 2.07 | 120 |
| 8 to 11 | 12.34 | 82.00 | 0.70 | 4.96 | 120 |
| 12 | 2.49 | 87.93 | 1.14 | 8.44 | 120 |
| 13 | 0 | 86.80 | 1.53 | 11.67 | 120 |

Comparative Example 6

In a 300 ml laboratory autoclave, 100 g of biphenyl were hydrogenated in the presence of 5 g of a catalyst comprising 0.5% of Ru on $Al_2O_3$ supports in the form of 4-6 mm spheres at a hydrogen pressure of 30 bar and a temperature of 120° C. while stirring. After a reaction time of 14.5 hours, the catalyst was filtered off. The reaction mixture obtained was analyzed by gas chromatography at the times indicated in table 6. The results reported in table 6 (in each case in GC-% by area) were obtained.

TABLE 6

| Running time [h] | Biphenyl | Phenyl-cyclo-hexane | Phenyl-cyclo-hexene | Bicyclohexyl | Temperature [° C.] |
|---|---|---|---|---|---|
| | | GC-% by area | | | |
| 10 | 27.68 | 64.97 | 0.74 | 6.52 | 120 |
| 12 | 14.22 | 75.76 | 1.08 | 8.87 | 120 |
| 13 | 5.69 | 81.11 | 1.45 | 11.74 | 120 |
| 14.5 | 1.14 | 80.33 | 2.01 | 16.52 | 120 |

Comparative Example 7

In a 300 ml laboratory autoclave, 100 g of biphenyl were hydrogenated in the presence of 5 g of a catalyst comprising 0.3% of Ru on $SiO_2$ in the form of 4-6 mm spheres at a hydrogen pressure of 40 bar and a temperature of 130° C. while stirring. After a reaction time of 5 hours, the catalyst was filtered off. The reaction mixture obtained was analyzed by gas chromatography at the times indicated in table 7. The results reported in table 7 (in each case in GC-% by area) were obtained.

TABLE 7

| Running time [h] | Biphenyl | Phenyl-cyclo-hexane | Phenyl-cyclo-hexene | Bicyclohexyl | Temperature [° C.] |
|---|---|---|---|---|---|
| | | GC-% by area | | | |
| 5 | 0.71 | 5.21 | 2.23 | 91.85 | 130 |
| Output | 0.07 | 0.09 | 0.09 | 99.56 | — |

Comparative Example 8

In a 300 ml laboratory autoclave, 100 g of biphenyl were hydrogenated in the presence of 5 g of a catalyst comprising Ru on $SiO_2$ in the form of 0.3% of Ru on $SiO_2$ in the form of 4-6 mm spheres at a hydrogen pressure of 10 bar and a temperature of 90° C. while stirring. After a reaction time of 23 hours, the catalyst was filtered off. The reaction mixture obtained was analyzed by gas chromatography at the times indicated in table 8. The results reported in table 8 (in each case in GC-% by area) were obtained.

TABLE 8

| Running time [h] | Biphenyl | Phenyl-cyclo-hexane | Phenyl-cyclo-hexene | Bicyclohexyl | Temperature [° C.] |
|---|---|---|---|---|---|
| | | GC-% by area | | | |
| 5 | 78.69 | 12.34 | 0.35 | 8.29 | 90 |
| 11 | 53.27 | 31.44 | 0.63 | 14.30 | 90 |
| 17 | 29.82 | 46.39 | 0.82 | 22.70 | 90 |
| 23 | 9.92 | 53.20 | 0.98 | 35.77 | 90 |
| Output | 8.34 | 53.55 | 0.95 | 37.04 | — |

Example 9

Distillation of Crude Phenylcyclohexane

Table 9 shows the results of the distillation of the crude output having the following composition 80.9% of phenylcyclohexane, 18.3% of bicyclohexyl and 0.86% of biphenyl (in each case in GC-% by weight) in a batch distillation in a 100 cm long, protectively heated rotating ribbon column (about 20 theoretical plates). The apparatus was equipped with a 0.1 l double-wall heart-shaped flask at the bottom and a vapor distributor. The vapor tube at the top was heated by means of heating tape and the condenser was operated at 2° C. The product mixture was fractionated at a reflux ratio of 5:1. For comparison, table 10 shows the results obtained in the distillation of the output which have the following composition 94.3% of phenylcyclohexane, 5.2% of bicyclohexyl (in each case in GC-% by weight) and comprised significantly less bicyclohexyl and gave a significantly larger amount of in-specification phenylcyclohexane.

To provide low-bicyclohexyl phenylcyclohexane, continuous experiments were carried out in a distillation column DN50 which was equipped with about 2.4 m of Sulzer DX packing (about 48 theoretical plates) and was operated at a pressure at the top of 10 mbar.

The product value obtained at the bottom in each case comprised over 98% of phenylcyclohexane at bicyclohexyl concentrations in the range from 0.2 to 0.7%. The bicyclohexyl content of the distillate ranged from 19 to 50% as a function of the reflux ratio (from 4:1 to 19:1). At higher reflux ratios (11:1 and more), distillation yields of up to 90% could be achieved.

TABLE 9

Batch distillation of phenylcyclohexane

| | | % of distillate | | Bicyclohexyl [RT 18.3] | | Phenycyclohexane [RT 27.9] | | Biphenyl [RT 39.8] | Remainder |
|---|---|---|---|---|---|---|---|---|---|
| Sample | Amount [g] | [% of fraction] | [total %] | [% by weight] | [% by area] | [% by weight] | [% by area] | [% by area] | [% by area] |
| Feed | 55.5 | | | 18.3 | 17.72 | 80.9 | 79.22 | 0.86 | 2.20 |
| Fraction 1 | 3.7 | 7% | 7% | 44.1 | 43.73 | 53.4 | 53.39 | 0 | 2.88 |
| Fraction 2 | 6.4 | 12% | 18% | 37.3 | 36.79 | 60.6 | 60.18 | 0 | 3.03 |
| Fraction 3 | 5.4 | 10% | 28% | 32.5 | 32.01 | 65.5 | 64.97 | 0 | 3.02 |
| Fraction 4 | 7.0 | 13% | 41% | 26.2 | 25.86 | 71.6 | 71.23 | 0 | 2.91 |
| Fraction 5 | 9.7 | 17% | 58% | 16.1 | 15.72 | 82.7 | 81.89 | 0 | 2.39 |
| Fraction 6 | 5.7 | 10% | 68% | 8.5 | 8.25 | 90.9 | 89.99 | 0.01 | 1.75 |
| Fraction 7 | 8.1 | 15% | 83% | 2.7 | 2.49 | 98.3 | 96.60 | 0.01 | 0.90 |
| Fraction 8 | 4.6 | 8% | 91% | 0.7 | 0.57 | 100.6 | 99.03 | 0.01 | 0.39 |
| Bottoms | 2.8 | 5% | 96% | 0.2 | 0.02 | 82.8 | 80.83 | 14.96 | 4.19 |

TABLE 10

| | Batch distillation of phenylcyclohexane | | | | | | |
|---|---|---|---|---|---|---|---|
| | | % of distillate | | Bicyclohexyl [RT 18.3] | | Phenycyclohexane [RT 27.9] | |
| Sample | Amount [g] | [% of fraction] | [total %] | [% by weight] | [% by area] | [% by weight] | [% by area] | Remainder [% by area] |
| Feed | 51.5 | | | 5.2 | 5.04 | 94.3 | 93.98 | 0.98 |
| Fraction 1 | 3.6 | 7% | 7% | 24.1 | 24.00 | 75.2 | 75.58 | 0.42 |
| Fraction 2 | 5.1 | 10% | 17% | 12.6 | 12.47 | 86.7 | 86.95 | 0.58 |
| Fraction 3 | 5.7 | 11% | 28% | 8.2 | 8.01 | 91.4 | 91.68 | 0.31 |
| Fraction 4 | 6.0 | 12% | 40% | 5.6 | 5.46 | 94.1 | 94.31 | 0.23 |
| Fraction 5 | 5.6 | 11% | 50% | 3.8 | 3.60 | 95.9 | 96.20 | 0.20 |
| Fraction 6 | 6.0 | 12% | 62% | 1.8 | 1.62 | 97.9 | 98.22 | 0.16 |
| Fraction 7 | 9.1 | 18% | 80% | 0.7 | 0.55 | 99.0 | 99.34 | 0.11 |
| Fraction 8 | 5.4 | 10% | 90% | 0.3 | 0.10 | 100.2 | 99.81 | 0.09 |
| Fraction 9 | 2.8 | 5% | 96% | 0.2 | 0.05 | 99.9 | 99.87 | 0.08 |
| Bottoms | 1.9 | 4% | 99% | 0.2 | 0 | 90.1 | 90.84 | 9.16 |

The invention claimed is:

1. A process for preparing a substituted or unsubstituted phenylcyclohexane of formula I

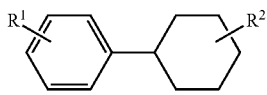

comprising catalytically hydrogenating a substituted or unsubstituted biphenyl of formula II

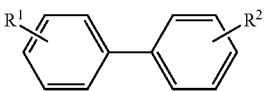

wherein:
$R^1$ is hydrogen and $R^2$ is hydrogen or phenyl, or
$R^1$ is a $C_1$-$C_4$-alkyl radical and $R^2$ is hydrogen, or
$R^1$ and $R^2$ are identical and are each phenyl or the same $C_1$-$C_4$-alkyl radical, and wherein
$R^1$ and $R^2$ are both simultaneously located in the respective ortho, meta or para positions of the two phenyl rings of the biphenyl of the formula II,
in the presence of hydrogen and a catalyst comprising
from 30 to 70% by weight of oxygen-comprising compounds of nickel, calculated as NiO,
from 15 to 45% by weight of oxygen-comprising compounds of zirconium, calculated as $ZrO_2$,
from 5 to 30% by weight of oxygen-comprising compounds of copper, calculated as CuO,
from 0.1 to 10% by weight of oxygen-comprising compounds of molybdenum, calculated as $MoO_3$, and
0 to 10% by weight of further components,
and wherein the figures in % by weight are based on a dry, unreduced catalyst.

2. The process according to claim 1, wherein $R^1$ and $R^2$ are each hydrogen.

3. The process according to claim 1, wherein the catalyst comprises
from 45 to 55% by weight of oxygen-comprising compounds of nickel, calculated as NiO,
from 25 to 35% by weight of oxygen-comprising compounds of zirconium, calculated as $ZrO_2$,
from 13 to 20% by weight of oxygen-comprising compounds of copper, calculated as CuO,
from 1 to 3% by weight of oxygen-comprising compounds of molybdenum, calculated as $MoO_3$, and
from 0 to 5% by weight of further components,
and wherein the figures in % by weight do not exceed 100% by weight.

4. The process according to claim 1, wherein the catalyst is in the form of a fixed-bed catalyst.

5. The process according to claim 1, wherein the hydrogenation is carried out at a hydrogen pressure in the range from 4 to 80 bar absolute.

6. The process according to claim 1, wherein the hydrogenation is carried out at a temperature in the range from 100 to 180° C.

7. The process according to claim 1, wherein the hydrogenation is carried out continuously.

8. The process according to claim 1, further comprising working up a reaction product obtained in the catalytic hydrogenation by distillation to purify the substituted or unsubstituted phenylcyclohexane of the formula I further.

9. The process according to claim 8, wherein the work-up by distillation of the reaction product from the catalytic hydrogenation is carried out under reduced pressure at absolute pressures in the range from 1 to 100 mbar.

10. The process according to claim 8, wherein fractions which are obtained in the work-up by distillation of the reaction product from the catalytic hydrogenation and still comprise biphenyl of the formula II are recirculated in their entirety or in part to the hydrogenation.

11. The process according to claim 1, wherein the hydrogenation is carried out so that from 90 to 95% of the substituted or unsubstituted biphenyl of the formula II is reacted.

12. The process according to claim 2, wherein the catalyst comprises:
from 45 to 55% by weight of oxygen-comprising compounds of nickel, calculated as NiO,
from 25 to 35% by weight of oxygen-comprising compounds of zirconium, calculated as $ZrO_2$,
from 13 to 20% by weight of oxygen-comprising compounds of copper, calculated as CuO,
from 1 to 3% by weight of oxygen-comprising compounds of molybdenum, calculated as $MoO_3$, and
from 0 to 5% by weight of further components, and wherein the figures in % by weight do not exceed 100% by weight.

13. The process according to claim 12, wherein the catalyst is in the form of a fixed-bed catalyst.

14. The process according to claim 13, wherein the hydrogenation is carried out at a hydrogen pressure in the range from 4 to 80 bar absolute.

15. The process according to claim 14, wherein the hydrogenation is carried out at a temperature in the range from 100 to 180° C.

16. The process according to claim 15, wherein the hydrogenation is carried out continuously.

* * * * *